(12) United States Patent
Appleton et al.

(10) Patent No.: US 8,884,078 B1
(45) Date of Patent: Nov. 11, 2014

(54) PROCESS FOR PRODUCING FATTY ALCOHOLS FROM FATTY ACIDS

(71) Applicant: Davy Process Technology Limited, London (GB)

(72) Inventors: Paul Appleton, Thornaby (GB); Michael Anthony Wood, Thornaby (GB); Robert Wild, Thornaby (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 13/884,815

(22) PCT Filed: Nov. 1, 2012

(86) PCT No.: PCT/GB2012/052726
§ 371 (c)(1),
(2), (4) Date: May 10, 2013

(87) PCT Pub. No.: WO2013/072664
PCT Pub. Date: May 23, 2013

(30) Foreign Application Priority Data

Nov. 17, 2011 (GB) .................................. 111987.1

(51) Int. Cl.
*C07C 29/128* (2006.01)
*C07C 29/149* (2006.01)
*C07C 31/125* (2006.01)

(52) U.S. Cl.
CPC ............ *C07C 29/1285* (2013.01); *C07C 29/149* (2013.01); *C07C 31/125* (2013.01); *C07C 29/128* (2013.01)
USPC .......................................... 568/877; 568/885

(58) Field of Classification Search
CPC .... C07C 29/128; C07C 29/149; C07C 31/125
USPC .................................................. 568/877, 885
See application file for complete search history.

(56) References Cited

U.S. PATENT DOCUMENTS 5,138,106 A * 8/1992 Wilmott et al. ............... 568/877
5,157,168 A * 10/1992 Wilmott et al. ............... 568/877

FOREIGN PATENT DOCUMENTS

DE 102007033636 A1 1/2009

OTHER PUBLICATIONS

International Search Report and Written Opinion for PCT/GB2012/052726, dated Jan. 23, 2013, 11 pages.

* cited by examiner

*Primary Examiner* — Elvis O Price
(74) *Attorney, Agent, or Firm* — Armstrong Teasdale LLP

(57) ABSTRACT

In a process for the production of fatty alcohol(s) a fatty acid or fatty acid mixture is subjected to esterification with a lower alkanol to form a stream comprising the corresponding lower alkyl ester or esters. The stream is vaporized and subjected to hydrogenation to form a stream comprising fatty alcohol(s) and an amount of unconverted lower alkyl ester(s). This stream is subjected to transesterification in a wax ester reactor in the presence of a solid transesterification catalyst. Fatty alcohol(s) and wax ester(s) are then separated by distillation to yield a fatty alcohol(s) product and a stream comprising wax ester(s). The stream of wax ester(s) is passed to a second hydrogenation zone to effect hydrogenation in the liquid phase to revert the wax ester(s) to fatty alcohol(s), which are returned to the distillation separation step.

22 Claims, 2 Drawing Sheets

PROCESS FOR PRODUCING FATTY ALCOHOLS FROM FATTY ACIDS

Figure 1:
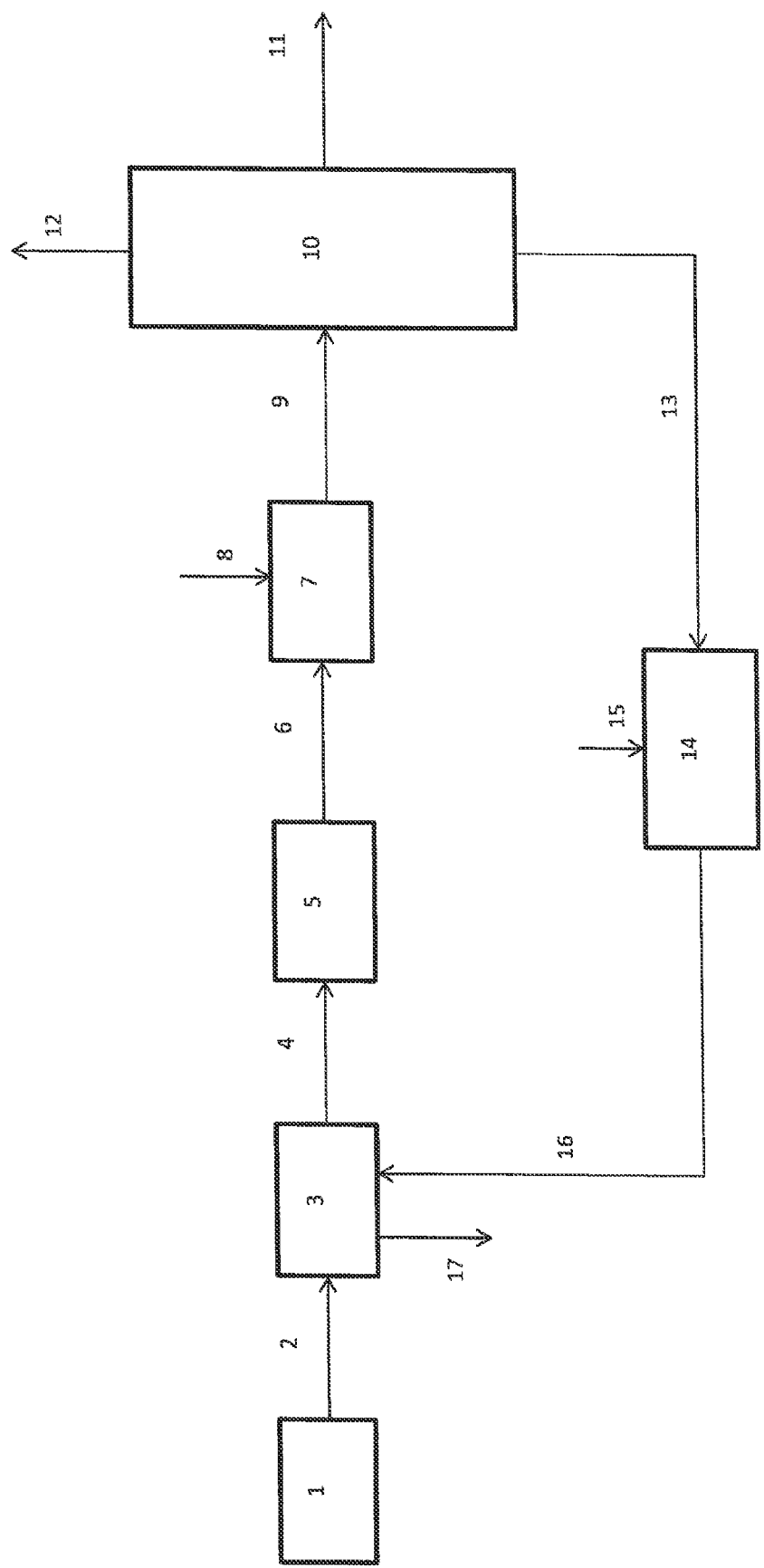

The present invention relates to a process for the production of fatty alcohols. More particularly, it relates to a process for the production of detergent fatty alcohols. Still more particularly, it relates to a process for the production and refining of fatty alcohol products obtained by the hydrogenation of esters.

Fatty alcohols, or higher alcohols as they are sometimes designated, are monohydric aliphatic alcohols containing six or more carbon atoms which are derived either from natural sources or are synthesised from petroleum feedstocks. They are often classified by their market usage. As the primary end use of primary alcohols containing between about 6 and about 11 carbon atoms is the production of plasticiser esters, such alcohols are often termed plasticiser alcohols. For higher alcohols containing, for example, from about 11 up to about 20 carbon atoms, the major use is the production of synthetic detergents, hence such alcohols are often termed detergent alcohols. The distinction between plasticiser alcohols and detergent alcohols is somewhat arbitrary and detergent alcohols may have from 10 carbon atoms. In addition, there is some production of phthalate esters from a $C_{13}$ "oxo" alcohol and also some production of, for example, non-ionic surfactants from $C_8$ to $C_{10}$ alcohols.

Although there are some natural products which contain esters which can be hydrogenated to produce alcohols in the plasticiser range, these are more usually produced synthetically from petroleum feedstocks by, for example, the so-called "oxo" process, a process which is also termed oxonation or hydroformylation. Detergent range alcohols, on the other hand, are typically produced by hydrogenation of low molecular alkyl esters of fatty acids. Such esters can be produced by transesterification of natural triglycerides or by esterification of the fatty acids obtained by hydrolysis of the triglycerides. Examples of triglycerides which can be used as raw materials include natural oils, such as coconut oil, rape seed oil, and palm oils, and animal fats such as lard, tallow, and fish oils. As such natural raw materials contain mixtures of triglycerides, the alcohol products obtained upon hydrogenation are also mixtures of n-alkanols of differing molecular weight. One process for carrying out the esterification is described in U.S. Pat. No. 5,536,856 the contents of which are incorporated herein by reference. In this process, the esterification of the fatty acid is carried out in a column reactor having a plurality of esterification trays, each having a predetermined liquid hold-up and containing a charge of a solid esterification catalyst. The fatty acid flows down the column reactor against an upflowing lower alkyl alcohol vapour stream such as methanol. The supplied alcohol is relatively dry and water of esterification is removed from the top of the column in the vapour stream. The product ester is recovered from the sump of the reactor. As the liquid flows down the trays it encounters progressively drier lower alkyl alcohol which drives the ester reaction towards 100% conversion. The ester may then be fed to a polishing reactor operated under liquid phase conditions.

Once produced, these esters can be hydrogenated to the desired alcohols. However, as discussed in detail in U.S. Pat. No. 5,138,106, the contents of which are incorporated herein by reference, there is a problem in refining the product alcohol mixtures because one or more of the alkyl esters in the ester mixture which is subjected to hydrogenation will generally have boiling points close to that of one of the product alcohols making separation of any unconverted alkyl esters from the product alcohol mixture extremely difficult if not impossible. The solution proposed in U.S. Pat. No. 5,138,106 is to use a process for recovering a fatty alcohol or alcohols from a fatty alcohol fraction containing a major molar amount of at least one fatty alcohol and a minor molar amount of at least one lower fatty acid ester comprising subjecting the fatty alcohol fraction to transesterification to convert substantially all of any lower alkyl fatty acid ester present in the feed mixture by ester interchange with a corresponding amount of fatty alcohol or alcohols to lower alkanol and to a wax ester derived from a fatty alcohol and a fatty acid. The lower alkanol is then separated from the reaction mixture by vaporization to yield an intermediate transesterification product mixture that contains a fatty alcohol or alcohols and a wax ester or esters. This mixture is then distilled to yield an overhead fraction that contains the fatty alcohol or alcohols and is substantially free from lower alkyl fatty acid ester, and a distillation residue comprising fatty alcohol or alcohols and wax ester or esters. This residue is then subjected to a second transesterification in the presence of added lower alkanol to reconvert wax ester or esters to lower alkyl fatty acid ester or esters and to fatty alcohol or alcohols. Unreacted lower alkanol is then evaporated from the reaction mixture. The fatty alcohol or alcohols and the lower alkyl fatty acid ester or esters can then be recycled.

An alternative process for the production of fatty alcohols is described in U.S. Pat. No. 5,157,168 the contents of which are incorporated herein by reference. In this process a fatty acid or mixture of fatty acids is esterified with a lower alkanol to form the corresponding fatty acid ester or esters. This ester or ester mix is then subjected to hydrogenation to give a product comprising a fatty acid or alcohols which are then refined. The conditions of both the esterification and the hydrogenation are selected such that the product stream is substantially free of ester.

A simplified version of one flow scheme for the production of fatty alcohols is illustrated schematically in FIG. 1. A fatty acid or mixture of fatty acids is subjected to esterification in the reactor 1. The product of the esterification reaction is withdrawn in line 2 and passed to vaporizer 3 where it is vaporized before being passed in line 4 to the hydrogenation reactor 5 where hydrogenation to desired alcohol occurs. The crude alcohol product generally has a residual alkyl ester content of about 2 to about 5 wt %. Although higher conversions may be achievable, this is coupled with a significant reduction in yield.

As discussed above, any residual ester can be particularly difficult to separate from the product alcohol and its presence can render the product of unacceptable purity for end users if the amount present is greater than about 0.15%. To address this, the product of the hydrogenation is then fed in line 6 to a wax ester reactor 7 where it is reacted in the presence of a liquid titania catalyst that is added in line 8. Here the residual ester, which is generally a methyl ester, is reacted with the product alcohol to form a wax ester via a homogeneously catalysed transesterification mechanism.

The product of the reaction is then passed in line 9 to the alcohol refining column 10 where the product alcohols can be separated readily from wax ester by conventional distillation. Product alcohols are removed in line 11. Lights are removed overhead in line 12 together with an alkane purge.

The residual wax ester could simply be removed. However, this would represent a loss to the economics of the process. The residual wax ester and the titania catalyst are therefore removed in line 13 and passed to a wax ester reversion reactor 14 where they are reacted with dry alcohol, such as methanol, added in line 15, in high molar excess. The wax ester is reversed back to the ester, such as the methyl ester, and product alcohol. The stream from the reversion reactor is then fed in line 16 to the vaporizer 3 where it is vaporized to separate the alcohol and the alkyl ester from the titania catalyst. A purge of heavies, including the titania catalyst, is removed from the vaporizer in line 17.

Although this arrangement does offer certain advantages over prior art process, several problems are encountered. First a liquid titinate catalyst is used in the reaction to form the wax ester. Whilst this catalyst is satisfactory it catalysing the reaction, it can become hydrolysed in the refining column 10 or in the reversion reactor 14. The hydrolysis is promoted by the presence of any water and although it is dry alcohol that is added to the reversion reactor 14 in line 15, it will still contain small amounts of water. If the catalyst is hydrolysed, $TiO_2$ can be deposited in the reversion reactor or the ester vaporizer. This is a problem as it requires the system to be shut down periodically so that the deposited $TiO_2$ can be removed. Even prior to the point at which shut down must occur to remove the deposited $TiO_2$ its build-up can lead to poor performance as the optimum flow paths become disturbed.

A further problem is that the reversion of wax ester to lower alcohol esters and the desired product alcohols can lead to a higher than desired alkane content in the crude alcohol product due to the recycle of alcohols in the reversion loop. This represents a reduction in overall process efficiency.

A still further problem relates to the lower alkanol added to the reversion reactor 14. This has to be essentially water free to reduce the hydrolysation issues. The need to use water free alkanol increases the costs of the reaction.

When the titanium catalyst has been hydrolysed it can no longer act to catalyse the transesterification of the wax ester to the lower alkyl ester and hence the conversion rate drops as hydrolysation occurs. If this reaction does have a poor conversion rate then the wax ester will not be reverted and will be lost from the process in the heavies purge taken from the vaporizer. This leads to a reduction in overall process efficiency.

A further problem relates to the alkane make. Akane is a by-product which is made across the hydrogenation reactor. As the heavies build so does the temperature required to vaporize the liquids and hence so does the temperature of the hydrogenation catalyst. This can lead to higher alkane make and hence loss of feed efficiency.

The growth in demand for naturally derived detergent range alcohols such as that derived from coconut or palm kernel oils has driven a desire to provide an improved process which addresses some, and preferably all, of the above problems.

It has now been found that the use of a solid transesterification catalyst in the wax ester reactor enables the flow sheet to be altered to use a liquid phase hydrogenation on the bottom stream from the alcohol refining. By this means any unconverted ester present as wax ester in the refining zone bottom stream can be converted to product alcohol and then be returned to the distillation zone for recovery. In addition, the heavies can be removed from the liquid phase hydrogenation step.

Thus according to the present invention there is provided a process for the production of fatty alcohol or alcohols comprising:
  (a) subjecting a fatty acid or fatty acid mixture to esterification with a lower alkanol in an esterification reactor maintained under esterification conditions to form a stream comprising the corresponding lower alkyl ester or esters;
  (b) vaporizing the stream from step (a);
  (c) subjecting the vaporized stream of step (b) to hydrogenation in a first hydrogenation zone operated under hydrogenation conditions to form a stream comprising fatty alcohol or alcohols and an amount of unconverted lower alkyl ester or esters;
  (d) subjecting the stream from step (c) to transesterification in a wax ester reactor maintained under transesterification conditions in the presence of a solid transesterification catalyst thereby to convert at least a portion of the lower alkyl fatty acid ester by ester interchange with a corresponding amount of fatty alcohol or alcohols to lower alkanol and to a wax ester or esters derived from a fatty alcohol and a fatty acid;
  (e) separating fatty alcohol or fatty alcohols and wax ester or wax esters of step (d) by distillation to yield a fatty alcohol or alcohols product and a stream comprising wax ester or esters;
  (f) passing said stream comprising wax ester or esters to a second hydrogenation zone operating under conditions to effect hydrogenation in the liquid phase to revert the wax ester or esters to fatty alcohol or alcohols; and
  (g) returning the fatty alcohol or alcohols to the separation step (e).

In one arrangement a heavies purge may be removed from the second hydrogenation zone. This purge may be passed to the vaporizer so that any product alcohol in the purge may be recovered.

The use of a solid transesterification catalyst in the wax ester reactor of step (d) and a liquid phase hydrogenation in step (f) allows at least a portion of any unreacted ester or esters from the hydrogenation step (c), and preferably all of any unreacted ester or esters from the hydrogenation step (c), to be converted into a wax ester or esters so that the ester or esters is not removed with the product alcohol or alcohols from the distillation step and then reverts the stream recovered from the distillation zone comprising the wax ester or esters to fatty alcohol or alcohols which can be recycled to the separating step (e). It should however be understood that the wax ester or esters stream recovered from the column bottoms of the refining step may comprise some fatty alcohol or alcohols.

This process of the present invention offers various advantages. One benefit is that the make of alkane is minimised. In addition the wax ester or esters formed is free of metal and can readily be reverted by liquid phase hydrogenation. A particularly important benefit of this process is that the use of solid catalyst in the wax ester reactor means that $TiO_2$ deposits are not formed in the reactors. A still further advantage is that a lower amount of heavies needs to be purged thereby minimising the losses from the system.

The term "fatty alcohol" means a linear alkanol containing from about 6 to about 26 carbon atoms. Preferred fatty alcohols contain from about 10 to about 20 carbon atoms. Thus in a preferred arrangement, the present invention relates to a process for the production of detergent fatty alcohols. Typical detergent fatty alcohols include hexanol, octanol, 1-decanol, 1-dodecanol, 1-tetradecanol, 1-hexadecanol, 1-octadecanol, 1-octadecenol and the like, and mixtures thereof.

The term "lower alkyl" means $C_1$- to $C_4$-alkyl, including methyl, ethyl, n-propyl, iso-propyl, n-butyl, iso-butyl and sec-butyl. The preferred lower alkyl radical is methyl. Similarly the term "lower alkanol" embraces $C_1$ to $C_4$ alkanols, including methanol, ethanol, n-propanol, iso-propanol, n-butanol, iso-butanol, and sec-butanol. Methanol is the preferred lower alkanol.

By the term "fatty acids" we mean linear saturated, unsaturated or polyunsaturated aliphatic acids, such as linear alkyl, alkenyl, or hydroxyalkenyl carboxylic acids containing from about 6 to about 26 carbon atoms, preferably about 10 to about 20 carbon atoms. Examples of such fatty acids are decanoic acid (capric acid), dodecanoic acid (lauric acid), tetradecanoic acid (myristic acid), pentadecanoic acid, hexadecanoic acid (palmitic acid), heptadecanoic acid (margaric acid), octadecanoic acid (stearic acid or isostearic acid), octadecenoic acids (oleic acid, linoleic acid or linolenic acid), hydroxyoctadecenoic acid (ricinoleic acid), eicosanoic acid (arachidic acid) and docosanoic acid (behenic acid). Mixtures of fatty acids are of especial importance as raw materials from which the lower alkyl fatty acid esters used as starting material in the hydrogenation step are prepared. Such mixtures of acids can be obtained by hydrolysis of naturally occurring triglycerides such as coconut oil, rape seed oil, palm oils, tallow, lard and fish oils. If desired, such mixtures of acids can be subjected to distillation to remove lower boiling acids having a lower boiling point than a chosen temperature and thus produce a "topped" mixture of acids, or to remove higher boiling acids having a boiling point higher than a second chosen temperature and thus produce a "tailed" mixture of acids, or to remove both lower and higher boiling acids and thus produce a "topped and tailed" mixture of acids.

In a preferred process of the present invention esterification of the fatty acid or fatty acid mixture with the lower alkanol (e.g. methanol) is effected by a procedure in which the fatty acid or fatty acid mixture and lower alkanol are passed in countercurrent flow through a column reactor provided with a plurality of esterification trays mounted one above another, each adapted to hold a predetermined liquid volume and a charge of solid esterification catalyst thereon, liquid downcomer means associated with each esterification tray adapted to allow liquid phase to pass down the column reactor from that esterification tray but to retain solid esterification catalyst thereon, and vapour upcomer means associated with each esterification tray adapted to allow vapour to enter that esterification tray from below and to agitate the mixture of liquid and solid esterification catalyst on that tray, in which the fatty acid or fatty acid mixture is supplied in liquid phase to the uppermost one of said plurality of esterification trays whilst the lower alkanol is supplied in vapour form beneath the lowermost one of said plurality of esterification trays, in which vapour comprising lower alkanol and water of esterification is recovered from an upper part of the column reactor, and in which a lower alkyl fatty acid ester or ester mixture is recovered from a lower part of the column reactor.

In such a procedure the water content of the lower alkanol vapour supplied to the column reactor should be less than about 5 mole % and the number of esterification trays and the reaction conditions should be selected so that the stream of lower alkyl fatty acid ester or esters has a low acid content of less than about 1 mole %, calculated on a lower alkanol free basis, and an ester content, also expressed on an alkanol free basis, of at least about 99 mole %.

The process of the invention utilises the vaporous stream of the lower alkanol to carry away water of esterification produced in the esterification reactor but without carrying with it significant quantities of the fatty acid or acids or of the lower alkyl fatty acid ester or esters.

Any suitable reaction conditions can be used for the esterification in the esterification reactor. The esterification conditions used in the column reactor will normally include use of elevated temperatures up to about 160° C., for example a temperature in the range of from about 80° C. to about 140° C., preferably in the range of from about 100° C. to about 125° C. Such operating temperatures will be determined by factors such as the thermal stability of the esterification catalyst, the kinetics of the esterification reaction and the vapour temperature of the lower alkanol fed to the base of the column reactor at the relevant inlet pressure. Typical operating pressures at the vapour inlet of the column reactor range from about 0.1 bar to about 25 bar. A liquid hourly space velocity through the column reactor in the range of from about $0.1 \text{ hr}^{-1}$ to about $10 \text{ hr}^{-1}$, typically from about $0.2 \text{ hr}^{-1}$ to about $5 \text{ hr}^{-1}$, or about $2 \text{ hr}^{-1}$ may be used.

The fatty acid or fatty acid mixture is supplied in liquid form to an upper part of the column reactor or in admixture with lower alkanol, in solution in recycled ester product, or in solution in an inert solvent or diluent therefor. It is possible to pre-react the lower alkanol and the fatty acid or fatty acid mixture prior to introduction to the column reactor. The resulting reaction mixture contains a mixture of lower alkyl fatty acid ester or ester mixture, water, and lower alkanol.

Generally a vaporous mixture exits the column reactor as an overhead product. Provision may be made for scrubbing such vaporous mixture with lower alkanol in liquid form in order to wash traces of fatty acid ester and of fatty acid back into the column reactor. This overhead product from the column reactor can be condensed and treated in known manner to separate its constituents, the recovered water of esterification being rejected and the lower alkanol being recycled for re-use in as dry a form as is practicable within the relevant economic constraints. The lower the water content of the lower alkanol vapour that is supplied to the lowermost one of said esterification trays, the further towards 100% conversion to ester the esterification equilibrium reaction can be driven and the lower the residual acidity of the ester containing product recovered from the bottom of the column reactor will be. However, a balance may often have to be struck between the cost of providing, for example, a substantially dry lower alkanol for vaporization into the column reactor, on the one hand, and the cost of providing and operating any additional downstream processing facilities that may be required to upgrade the ester product to the required quality if a less dry alkanol is used. This will vary from lower alkanol to lower alkanol and will depend upon the interaction between water and lower alkanol (e.g. azeotrope formation) and its effect upon alkanol/water separation. In any case, the water content of the lower alkanol vapour supplied to the reactor is less than about 5 mole %, and even more preferably is less than about 1 mole %.

The column reactor has a plurality of esterification trays. Although two or three trays may suffice in some cases, it will typically be necessary to provide at least about 5 up to about 20 or more esterification trays in the column reactor. Typically each esterification tray is designed to provide a residence time for liquid on each tray of from about 1 minute up to about 120 minutes, preferably from about 5 minutes to about 60 minutes.

A catalyst will generally be used for the esterification and this will generally be a solid catalyst. The solid esterification catalyst may be a granular ion exchange resin containing $SO_3H$ and/or $COOH$ groups. Macroreticular resins of this type are preferred. Examples of suitable resins are those sold under the trade marks "Amberlyst", "Dowex", "Dow" and "Purolite", such as Amberlyst 13, Amberlyst 66, Dow C351 and Purolite C150.

Different solid esterification catalysts may be used on different trays of the column reactor. Moreover different concentrations of solid esterification catalyst can be used on different trays.

The charge of solid particulate or granular esterification catalyst on each tray is typically sufficient to provide a catalyst to liquid ratio on that tray corresponding to a resin concentration of at least about 0.2% w/v for example, a resin concentration in the range of from about 2% w/v to about 20% w/v, preferably 5% w/v to 10% w/v, calculated as dry resin. Sufficient catalyst should be used to enable equilibrium or near equilibrium conditions to be established on the tray within the selected residence time at the relevant operating conditions. On the other hand not so much catalyst should be used on each tray that it becomes difficult to maintain the catalyst in suspension in the liquid on the tray by the agitation produced by the upflowing vapour entering the tray from below. For a typical resin catalyst a resin concentration in the range of from about 2% v/v to about 20% v/v, preferably 5% v/v to 10% v/v may be used.

The particle size of the catalyst should be large enough to facilitate retention of the catalyst on each tray by means of a screen or similar device. However, as larger catalyst particle sizes are more difficult to maintain in suspension and have lower geometrical surface area per gram, it is expedient to use not too large a catalyst particle size. A suitable catalyst particle size is in the range of from about 0.1 mm to about 5 mm.

Whilst a catalyst will generally be used for the esterification reaction, in one arrangement it may be autocatalysed.

One or more wash trays may be provided above the esterification trays in order to prevent loss of product, solvent and/or reagents from the column reactor.

In the first hydrogenation zone of the process of the invention the lower alkyl fatty acid ester or esters are hydrogenated under vapour phase hydrogenation conditions in which the composition of the gas stream is selected so that at all times the material in contact with the hydrogenation catalyst is above the dew point, preferably at least about 5° C. above the dew point. Typical vapour phase hydrogenation conditions include use of temperatures of up to about 260° C., such as temperatures in the range of from about 14° C. to about 240° C., and pressures in the range of from about 5 bar to about 100 bar. Typically the hydrogen:ester mole ratio in the vaporous feed to the hydrogenation zone is at least about 100:1 up to about 2000:1 or more.

Suitable hydrogenation catalysts include ester hydrogenation catalysts such as reduced copper oxide-zinc oxide catalysts such as those described in GB2116552 and WO82/03854, and copper chromite, and promoted copper chromite catalysts. The preferred catalysts are reduced copper oxide-zinc oxide catalysts of the type disclosed in GB2116552 and WO82/03854. Such catalysts include reduced mixtures of copper oxide and zinc oxide derived from mixtures comprising, before reduction, (a) from about 10 to about 70 percent by weight CuO and about 90 to about 30 percent by weight ZnO, (b) from about 65 to about 85 percent by weight CuO and about 15 to about 35 percent by weight ZnO, and (c) from about 40 to about 50 percent by weight each of CuO and ZnO and 0 to 20 percent by weight of alumina. The preferred copper chromite catalysts are those containing from about 25 to about 45 percent by weight of copper and from about 20 to about 35 percent by weight of chromium, calculated as metal.

The hydrogenation mixture obtained by hydrogenating a lower alkyl fatty acid ester or mixture of esters contains, in addition to a fatty alcohol or fatty alcohol mixture, also lower alkanol, such as methanol. The lower alkanol is separated by any suitable means, such as by distillation in one or more stages, from the fatty alcohol or alcohols to yield a fatty alcohol fraction suitable for use in the process of the invention. Such a fatty alcohol fraction typically contains, besides possibly a minor molar amount of methanol or other lower alkanol, usually less than about 5 mole %, a major molar amount of a fatty alcohol or alcohols, usually about 90 mole % or more, and a minor molar amount of unreacted lower alkyl fatty acid ester or esters, usually from about 0.5 mole % up to about 5 mole %.

In the first hydrogenation step of the process of the invention vapour phase conditions are used. In order to maintain all components in the vapour phase two important factors are (a) the hydrogen:ester molar ratio of the vaporous mixture to the hydrogenation zone and (b) the temperature thereof. In general, the higher the molecular weight of the lower alkyl fatty acid ester is, the less volatile it is and the higher its boiling point. Hence, for example, when using methyl laurate as a feedstock to the hydrogenation zone, a lower hydrogen:ester molar ratio and a lower inlet temperature to the hydrogenation zone can be used than when a higher boiling ester, such as methyl stearate, is to be hydrogenated. In practice a plant operator may wish to have the freedom to operate the process using fatty acids derived from different sources at different times. For example, he may wish to operate at different times using fatty acids from any of the common sources, such as tallow, lard, fish oil, coconut oil, rape seed oil or palm oil. A plant capable of handling such a range of acid feedstocks must be capable of hydrogenating the highest boiling methyl or other lower alkyl ester of a fatty acid that is likely to be used. Hence it must have an ester vaporization section that can operate over a range of $H_2$:ester molar ratios and that can deliver to the hydrogenation zone a vaporous inlet mixture at the appropriate temperature, i.e. a higher inlet temperature and a higher $H_2$:ester molar ratio for methyl stearate, for example, than for methyl laurate.

The hydrogenation zone may comprise a single reactor operated under adiabatic conditions and containing a single bed of an ester hydrogenation catalyst, such as copper chromite or a reduced CuO—ZnO catalyst. In this case, however, the bed of catalyst must be sized so as to enable hydrogenation to be completed so far as possible by a single passage of the vaporous mixture therethrough at the design feed rate when operating at the lowest design temperature. In addition provision has to be made in designing the plant for any catalyst deactivation that may occur with ageing of the catalyst. If this approach is adopted then, with a catalyst charge that is sized for operation at a temperature suitable for a relatively low boiling ester, such as methyl laurate, it will be understood that, at the higher operating temperatures and higher hydrogen:ester molar ratios needed to maintain a high boiling ester, such as methyl stearate, in the vapour phase, hydrogenation occurs faster so that it is mainly the front end of the catalyst bed that is playing a part in the hydrogenation reactor, whilst the back end of the catalyst bed plays essentially no part. A disadvantage of this design approach is that, when operating with a high boiling ester, such as methyl stearate, the hot reaction mixture remains in contact with the catalyst for a significant time at the back end of the catalyst bed, although the hydrogenation reaction has effectively gone to completion, with the result that the conversion to by-products is correspondingly higher.

To address this, the first hydrogenation zone may have a plurality of beds, or sections of catalyst bed, of hydrogenation catalyst arranged in series which can be brought into use as required. In one arrangement the first hydrogenation zone has a main inlet and a main outlet, a plurality of beds of hydrogenation catalyst in the path of gas flowing between the main inlet and the main outlet, and one or more secondary flow connections each located between a respective pair of catalyst beds. The vaporous mixture containing hydrogen and lower alkyl fatty acid ester can be fed to the hydrogenation reactor by means of the main inlet whilst the reaction product is withdrawn either via the main outlet, so that all of the catalyst beds are used, or via one of the secondary flow connections, so that one or some only of the catalyst beds is or are used, depending upon the volatility of the ester, and hence upon the hydrogen:ester molar ratio and the inlet temperature of the vaporous mixture. Alternatively the reaction mixture can be withdrawn from the main outlet whilst the vaporous mixture is fed to one of the secondary flow connections. Any catalyst beds which are not in active use are maintained under an appropriate pressure of hydrogen. In this way the plant operator can readily select the appropriate number of beds of catalyst to suit the nature of the fatty acid feedstock currently being used.

The product of the hydrogenation is then passed to a wax ester reactor where transesterification to the wax ester occurs. The reaction is carried out in the presence of a solid transesterification catalyst. Any suitable transesterification catalyst may be used. Suitable catalysts include titanium silicate, cationic resins, zinc lanthanides, tungsten oxide on silica, zirconium sulphide, titanium based catalysts supported on cerium oxide or magnesium oxide. Further examples of suitable catalysts include "Amberlyst 15", "Amberlyst 16" or in the acid (R—SO$_3$H) and salt (R—SO$_3$Na) form of a sulphonic group or a carboxylic acid group. Further examples of suitable catalysts can be found in U.S. Pat. No. 4,681,967, EP0523461, EP0646567, U.S. Pat. No. 5,561,205, U.S. Pat. No. 5,436,357, WO98/28256, EP096487, EP0781758, WO99/47483, U.S. Pat. No. 6,204,424, U.S. Pat. No. 6,316,654, U.S. Pat. No. 6,359,157, U.S. Pat. No. 6,933,398, WO06/029655, U.S. Pat. No. 6,376,701, U.S. Pat. No. 6,743,942, WO07/043,062, WO03/020782, WO07/111,604, U.S. Pat. No. 7,030,057, WO04/085583, U.S. Pat. No. 7,211,681, EP1640356, WO06/070661, WO05/100306, U.S. Pat. No. 6,979,748, U.S. Pat. No. 7,078,560, U.S. Pat. No. 7,122,688, US2008/0021232, WO06/129435, WO07/074,592, WO06/133437, WO07/025,360, EP1785478, WO06/050925, US59088463, U.S. Pat. No. 6,147,196, WO07/006,569, and WO06/013080 which are incorporated herein by reference.

The tranesterification conditions will, to a large extent, depend upon the catalyst chosen. In one arrangement it may be carried out at a temperature of from about 150° C. to about 250° C. A pressure in the range of from about 2 psia to about 100 psia may be used with a pressure in the region of about 5 psia to about 50 psia being particularly useful. In one arrangement the catalyst may be in a fixed bed with a residence time of about 1 to about 5 hours.

The distillation of the substantially lower alkanol free mixture to yield a product alcohol stream and a distillation residue and optionally with lights removal, is normally effected at or near atmospheric pressure or below, for example at a pressure in the range of from about 0.005 bar to about 1.2 bar. The reactor in which the distillation occurs may be of any suitable configuration.

The crude product liquid containing fatty alcohols, wax esters, catalyst and impurities will generally be passed to a refining column. The refining column will be operated under any suitable conditions. In one arrangement, the column operates under a vacuum at about 0.03 bara and uses structured packing. In one arrangement the middle sections of the column may contain a divided wall to separate the feed and product draws.

A purge stream may be removed as a liquid overhead product. This stream will contain light impurities such as alkane by-products from the hydrogenation. Alkanol and other non-condensables present in the refining column feed may be removed in the vapour stream to the vacuum system. This vacuum system will generally provide the required vacuum for the column and may also be used to condense the alkanol rich vent from the transesterification reactor. In one arrangement, the overheads from the refining column may be condensed in two stages with both exchangers providing reflux to the column. Product alkanols will generally be removed as a side draw.

The distillation residue is subjected to liquid phase hydrogenation in a second hydrogenation zone. The wax esters are hydrogenated on a fixed bed of catalyst typically consisting of components such as copper or copper-chromium oxide with secondary components such as zinc, aluminium, iron, silicon, and alkaline earth elements. The hydrogenation will be carried out at any suitable conditions. In one arrangement, the temperature will be from about 180° C. to about 220° C. and a hydrogen pressure of from about 40 to about 100 bar.

Figure 2:
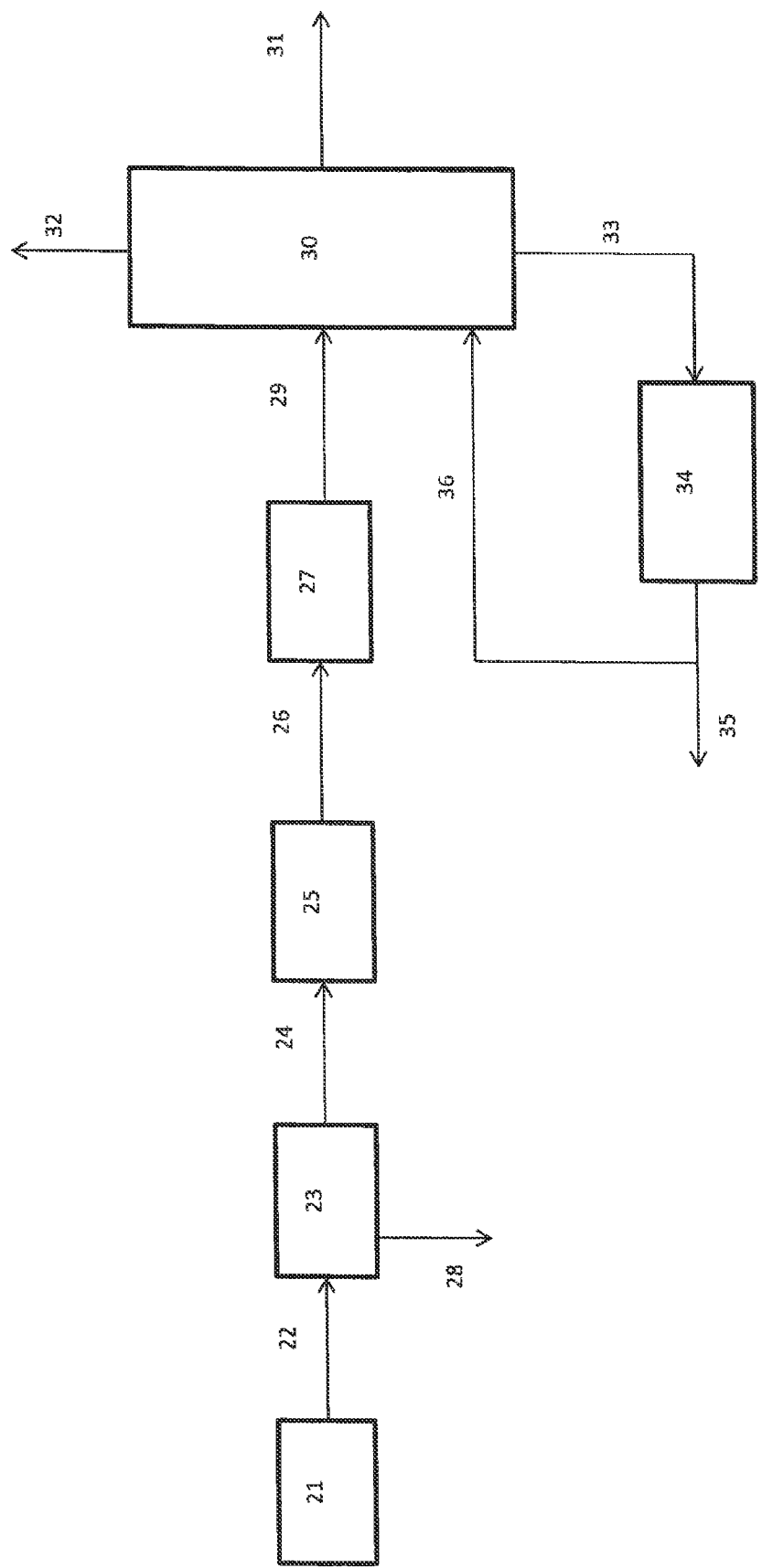

The present invention will now be described by way of example with reference to the accompanying figures in which:

FIG. 1 is a schematic representation of a process according to the prior art; and FIG. 2 is a schematic representation of the process of the present invention.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

A simplified version of a flow scheme of the present invention is illustrated schematically in FIG. 2. A fatty acid or mixture of fatty acids is subjected to esterification in the reactor 21. The product of the esterification reaction is withdrawn in line 22 and passed to vaporizer 23 where it is vaporized. A purge of heavies may be removed in line 28. The vaporized stream is passed in line 24 to the hydrogenation reactor 25 where hydrogenation to the desired alcohol occurs. The crude alcohol product generally has a residual lower alkyl ester content of about 2 to about 5 wt %. Although higher conversions may be achievable, this is coupled with a significant reduction in yield.

As discussed above, any residual ester can be particularly difficult to separate from the product alcohol and its presence can render the product of unacceptable purity for end users if the amount present is greater than about 0.15%. To address this, the product of the hydrogenation is then fed in line 26 to a wax ester reactor 27 where it is reacted in the presence of a solid transesterification catalyst. Here the residual ester, which is generally a methyl ester, is reacted with the product alcohol to form a wax ester via a heterogeneously catalysed transesterification mechanism.

The product of the reaction is then passed in line 29 to the alcohol refining column 30 where the product alcohols can be separated readily from wax ester by conventional distillation. Product alcohols are removed in line 31. Lights are removed overhead in line 32 together with an alkane purge.

The residual wax ester could simply be removed. However, this would represent a loss to the economics of the process. The residual wax ester are therefore removed in line 33 and passed to a liquid hydrogenation zone 34 which may be passed to vaporizer 23 to recover any product alcohol. Here the wax ester is converted to product alcohols. The stream 36 from the hydrogenation zone 34 is returned to the alcohol refining column 30. A purge 35 may also be taken from the hydrogenation zone 34.

The present invention will now be described with reference to the following examples.

Example 1

A standard 300 ml autoclave with a bottom drain point was assembled, with a sample bomb to allow the addition of liquid at operating temperature and pressure. Also a static catalyst basket was fashioned to allow the solid catalyst titania on silica (TiS) known as catalyst-1 to be held in the liquid contents of the autoclave.

2 g of the catalyst-1 was added to the basket and 200 mls of 1-dodecanol (157.9 g ex Aldrich) was added to the vessel. The autoclave was heated to 215° C. over 1 hour and 2 g of methyl laurate (ex Aldrich) added via the sample bomb which had been pressurised with nitrogen. The excess nitrogen pressure was then vented and the autoclave sealed. The contents were then sampled with time via the bottom drain valve after first taking a small purge.

Examples 2 to 6

Repeat tests were then performed using the same catalyst charge. Example 2 was identical to Example 1 to check for gross deactivation. Examples 3 and 4 used double the methyl laurate concentration, Example 5 decreased the stirrer speed to check for mass transfer limitations and Examples 4, 5 and 6 had 4 wt % methanol added to the initial pot contents. Example 6 was performed at pressure (52 psig)

Tables 1-6 show the progress of the reaction with time.

TABLE 1

Example 1

| Time (mins) | $C_{12}$ Ester Conversion (wt %) |
|---|---|
| 0 | 0 |
| 5 | 2.75 |
| 10 | 8.26 |
| 15 | 11.93 |
| 30 | 25.69 |
| 60 | 44.04 |
| 1440 | 100 |

TABLE 2

Example 2

| Time (mins) | $C_{12}$ Ester Conversion (wt %) |
|---|---|
| 0 | 0 |
| 10 | 0.48 |
| 20 | 3.79 |
| 30 | 10.48 |
| 45 | 25.24 |
| 60 | 37.28 |
| 100 | 65.14 |
| 120 | 75.63 |
| 180 | 91.46 |
| 1200 | 97.77 |
| 1260 | 98.16 |

TABLE 3

Example 3

| Time (mins) | $C_{12}$ Ester Conversion (wt %) |
|---|---|
| 0 | 0 |
| 15 | 5.45 |
| 30 | 16.12 |
| 45 | 25.88 |
| 65 | 38.61 |
| 215 | 55.6 |
| 245 | 70.94 |
| 300 | 84.36 |
| 370 | 92.16 |
| 1500 | 98.34 |

TABLE 4

Example 4

| Time (mins) | $C_{12}$ Ester Conversion (wt %) |
|---|---|
| 0 | 0 |
| 15 | 11.18 |
| 30 | 31.37 |
| 60 | 63.55 |
| 90 | 83.06 |
| 125 | 91.38 |
| 185 | 94.07 |
| 240 | 94.32 |
| 1260 | 94.54 |

TABLE 5

Example 5

| Time (mins) | $C_{12}$ Ester Conversion (wt %) |
|---|---|
| 0 | 0 |
| 15 | 14.45 |
| 30 | 33.04 |
| 60 | 64.79 |
| 90 | 82.18 |
| 120 | 87.98 |
| 180 | 89.9 |

TABLE 6

Example 6

| Time (mins) | $C_{12}$ Ester Conversion (wt %) |
|---|---|
| 0 | 0 |
| 15 | 9.68 |
| 30 | 20.09 |
| 45 | 30.14 |
| 60 | 35.45 |
| 90 | 49.64 |
| 120 | 57.43 |
| 150 | 63.42 |
| 180 | 67.52 |
| 210 | 71.35 |
| 1200 | 72.75 |

Example 7

192 g dodecanol ($C_{12}$-OL) and 8 g methyl laurate (MeL) were charged to a 500 mL round-bottomed flask, nitrogen purged and heated to the desired reaction temperature, at which point 20 g catalyst was added and the reaction flask sampled periodically. Methanol was continuously removed from the mixture by means of an overheads condenser.

Methyl laurate removal test using TiS catalyst. Conditions: 170° C., 100 rpm stirrer, under N2. Details are set out in Table 7

TABLE 7

| Time (mins) | $C_{12}$ Ester Conversion (wt %) |
| --- | --- |
| 0 | 0 |
| 30 | 15.10 |
| 60 | 27.04 |
| 120 | 42.30 |
| 180 | 48.21 |
| 240 | 54.61 |
| 300 | 62.79 |
| 360 | 69.12 |
| 440 | 75.80 |
| 480 | 77.72 |

Example 8

Transesterification testwork that required elevated pressure was undertaken in a 300 mL static basket autoclave with a gas-induction impeller. Catalyst was nominally charged to the shell of the static basket and the autoclave fitted with an overhead condenser to remove methanol from the reactor. 15 g of catalyst was charged to the basket along with 144 g $C_{12}$-OL and 6 g MeL and the autoclave nitrogen blanketed. Reaction time started when the autoclave reached the desired reaction temperature and periodic samples taken via a dip tube.

Methyl laurate removal test using TiS. Conditions: 170° C., 250 rpm stirrer, under 50 psig $H_2$. Details are set out in Table 8

TABLE 8

| Time (mins) | $C_{12}$ Ester Conversion (wt %) |
| --- | --- |
| 0 | 0 |
| 60 | 1.69 |
| 120 | 7.92 |
| 210 | 14.73 |
| 280 | 31.80 |
| 350 | 41.70 |
| 460 | 55.94 |
| 660 | 70.90 |
| 875 | 87.16 |

Examples 9 and 10

192 g dodecanol and 1 g catalyst were charged in a 500 mL multi-neck flask with overhead stirrer, condenser and liquid thermocouple (standard transesterification glassware setup) and heated up to 180° C. under a nitrogen atmosphere and stirred at 300 rpm. When it had reached the desired temperature, 8 g methyl laurate was quickly added and the test started. A sample was taken shortly after addition of methyl laurate (T=0), thereafter samples were taken every 15 minutes for the first hour, then every half hour, hourly and every four hours until >95% conversion was reached. Samples were analysed by GC.

In Example 9 the catalyst was Ti/Ce and in Example 10 the catalyst was Ti/Mg.

The results of Example 9 are summarized in Table 9.

TABLE 9

| Time, min. | MeOH, wt % | C12 OL, wt % | C12 Ester, wt % | C24 Wax ester, wt % |
| --- | --- | --- | --- | --- |
| 0 | 0.097 | 94.838 | 4.048 | 0.067 |
| 15 | 0.101 | 94.515 | 3.467 | 0.953 |
| 30 | 0.126 | 94.140 | 2.957 | 1.802 |
| 45 | 0.162 | 93.774 | 2.464 | 2.619 |
| 60 | 0.186 | 93.452 | 2.034 | 3.330 |
| 90 | 0.211 | 93.035 | 1.380 | 4.355 |
| 120 | 0.220 | 92.602 | 0.958 | 5.165 |
| 180 | 0.201 | 92.148 | 0.518 | 6.030 |
| 210 | 0.189 | 92.094 | 0.368 | 6.216 |
| 240 | 0.172 | 92.034 | 0.298 | 6.341 |
| 300 | 0.174 | 91.887 | 0.192 | 6.544 |
| 360 | 0.170 | 91.825 | 0.127 | 6.630 |
| 420 | 0.163 | 91.698 | 0.100 | 6.745 |
| 480 | 0.127 | 91.657 | 0.082 | 6.808 |
| 720 | 0.105 | 91.545 | 0.051 | 6.914 |
| 960 | 0.081 | 91.445 | 0.040 | 6.971 |
| 1200 | 0.065 | 91.445 | 0.031 | 6.944 |

In Example 9, the catalyst reached >95% (95.26%) conversion after T=300. Only one run was performed and no repeats.

The results of Example 10 are summarized in Table 10.

TABLE 10

| Time, min. | MeOH, wt % | C12 OL, wt % | C12 Ester, wt % | C24 Wax ester, wt % |
| --- | --- | --- | --- | --- |
| 0 | 0.028 | 94.764 | 3.931 | 0.154 |
| 15 | 0.101 | 94.494 | 3.661 | 0.703 |
| 30 | 0.107 | 94.213 | 3.211 | 1.344 |
| 45 | 0.171 | 93.875 | 2.812 | 1.998 |
| 60 | 0.142 | 93.810 | 2.446 | 2.620 |
| 90 | 0.194 | 93.288 | 1.811 | 3.694 |
| 120 | 0.209 | 92.865 | 1.317 | 4.567 |
| 180 | 0.301 | 92.348 | 0.676 | 5.531 |
| 240 | 0.264 | 92.004 | 0.355 | 6.151 |
| 300 | 0.184 | 91.918 | 0.200 | 6.461 |
| 360 | 0.152 | 91.982 | 0.124 | 6.475 |
| 420 | 0.218 | 91.749 | 0.115 | 6.502 |
| 480 | 0.136 | 91.922 | 0.072 | 6.570 |
| 720 | 0.099 | 91.898 | 0.047 | 6.591 |
| 960 | 0.063 | 91.790 | 0.040 | 6.651 |
| 1200 | 0.052 | 91.796 | 0.030 | 6.611 |

The catalyst of Example 10 reached ~95% conversion (94.88%) after T=300. Only one run was performed, no repeats.

The invention claimed is:

1. A process for the production of fatty alcohol or alcohols comprising:
   (a) subjecting a fatty acid or fatty acid mixture to esterification with a lower alkanol in an esterification reactor maintained under esterification conditions to form a stream comprising the corresponding lower alkyl ester or esters;
   (b) vaporizing the stream from step (a);
   (c) subjecting the vaporized stream of step (b) to hydrogenation in a first hydrogenation zone operated under hydrogenation conditions to form a stream comprising fatty alcohol or alcohols and an amount of unconverted lower alkyl ester or esters;

(d) subjecting the stream from step (c) to transesterification in a wax ester reactor maintained under transesterification conditions in the presence of a solid transesterification catalyst thereby to convert at least a portion of the lower alkyl fatty acid ester by ester interchange with a corresponding amount of fatty alcohol or alcohols to lower alkanol and to a wax ester or esters derived from a fatty alcohol and a fatty acid;

(e) separating fatty alcohol or fatty alcohols and wax ester or wax esters of step (d) by distillation to yield a fatty alcohol or alcohols product and a stream comprising wax ester or esters;

(f) passing said stream comprising wax ester or esters to a second hydrogenation zone operating under conditions to effect hydrogenation in the liquid phase to revert the wax ester or esters to fatty alcohol or alcohols; and (g) returning the fatty alcohol or alcohols to the separation step (e).

2. A process according to claim 1 wherein a heavies purge is removed from the second hydrogenation zone and optionally passed to the vaporizer in which step (b) occurs.

3. A process according to claim 1 wherein the fatty alcohol contains from about 6 to about 20 carbon atoms.

4. A process according to claim 1 wherein the esterification reactor is a column reactor and esterification of the fatty acid or fatty acid mixture with the lower alkanol is effected by passing the fatty acid or fatty acid mixture and lower alkanol in countercurrent flow through the column reactor.

5. A process according to claim 4 wherein the column reactor is provided with: a plurality of esterification trays mounted one above another, each adapted to hold a predetermined liquid volume and a charge of solid esterification catalyst thereon; liquid downcomer means associated with each esterification tray adapted to allow liquid phase to pass down the column reactor from that esterification tray but to retain solid esterification catalyst thereon; and vapour upcomer means associated with each esterification tray adapted to allow vapour to enter that esterification tray from below and to agitate the mixture of liquid and solid esterification catalyst on that tray.

6. A process according to claim 1 wherein the temperature of the esterification in the esterification reactor is up to about 160° C., or from about 80° C. to about 140° C., or from about 100° C. to about 125° C.

7. A process according to claim 1 wherein the pressure at a vapour inlet of the esterification reactor is from about 0.1 bar to about 25 bar.

8. A process according to claim 1 wherein the liquid hourly space velocity through the esterification reactor is from about 0.1 hr−1 to about 10 hr−1, or from about 0.2 hr−1 to about 5 hr−1 or about 2 hr−1.

9. A process according to claim 1 wherein the esterification is carried out in the presence of a solid esterification catalyst comprising a granular ion exchange resin containing SO3H and/or COOH groups.

10. A process according to claim 1 wherein the hydrogenation conditions in the first hydrogenation zone are such that material in contact with a hydrogenation catalyst is above the dew point.

11. A process according to claim 1 wherein a catalyst present in the first hydrogenation zone is selected from reduced copper oxide-zinc oxide catalysts, copper chromite, and promoted copper chromite catalysts.

12. A process according to claim 1 wherein the temperature in the first hydrogenation zone is up to about 260° C.

13. A process according to claim 1 wherein the pressure in the first hydrogenation zone is from about 5 bar to about 100 bar.

14. A process according to claim 1 to wherein the hydrogen:ester mole ratio in the vaporous feed to the first hydrogenation zone is at least about 100:1 up to about 2000:1 or more.

15. A process according to any claim 1 wherein the transesterification is carried out in the presence of a solid transesterification catalyst selected from titanium silicate, cationic resins, zinc lanthanides, tungsten oxide on silica, zirconium sulphide, titanium based catalysts supported on cerium oxide or magnesium oxide.

16. A process according to claim 1 wherein the transesterification is carried out at a temperature of from about 150° C. to about 250° C.

17. A process according to claim 1 wherein the transesterification is carried out at a pressure of from about 5 psig to about 100 psig.

18. A process according to claim 1 wherein the transesterification is carried out in the presence of a catalyst in a fixed bed with a residence time of about 1 to about 5 hours.

19. A process according to claim 1 wherein the distillation is carried out at a pressure of from about 0.005 bar to about 1.2 bar.

20. A process according to claim 1 wherein a catalyst is present in the second hydrogenation zone selected from catalysts consisting of copper or copper-chromium oxide with zinc, aluminium, iron, silicon, or alkaline earth elements.

21. A process according to claim 1 wherein the temperature in the second hydrogenation zone is from about 180° C. to about 220° C.

22. A process according to claim 1 wherein the hydrogen pressure in the second hydrogenation zone is of from about 40 to about 100 bar.

* * * * *